(12) United States Patent
Brosig et al.

(10) Patent No.: US 10,758,643 B2
(45) Date of Patent: Sep. 1, 2020

(54) MECHANOPHORIC MEDICAL PRODUCT

(71) Applicant: Aesculap AG, Tuttlingen (DE)

(72) Inventors: Kris Brosig, Plüderhausen (DE);
Michael Utz, Tuttlingen (DE)

(73) Assignee: Aesculap AG, Tuttlingen (DE)

( * ) Notice: Subject to any disclaimer, the term of this patent is extended or adjusted under 35 U.S.C. 154(b) by 222 days.

(21) Appl. No.: 15/516,864

(22) PCT Filed: Aug. 3, 2016

(86) PCT No.: PCT/EP2016/068540
§ 371 (c)(1),
(2) Date: Apr. 4, 2017

(87) PCT Pub. No.: WO2017/025408
PCT Pub. Date: Feb. 16, 2017

(65) Prior Publication Data
US 2019/0151502 A1 May 23, 2019

(30) Foreign Application Priority Data

Aug. 7, 2015 (DE) .................. 10 2015 215 112
Feb. 29, 2016 (DE) .................. 10 2016 203 287

(51) Int. Cl.
*A61L 27/28* (2006.01)
*A61L 27/50* (2006.01)
(Continued)

(52) U.S. Cl.
CPC ............ *A61L 27/28* (2013.01); *A61B 17/025* (2013.01); *A61B 17/0206* (2013.01); *A61F 2/30767* (2013.01); *A61L 27/50* (2013.01); *A61L 29/14* (2013.01); *A61L 31/08* (2013.01); *A61L 31/14* (2013.01); *A61B 2017/0275* (2013.01);
(Continued)

(58) Field of Classification Search
CPC .......... A61L 27/28; A61L 27/50; A61L 29/14; A61L 31/08; A61L 31/14; A61B 17/0206; A61B 17/025; A61F 2002/30047; A61F 2250/005; A61F 2250/0097; B41M 5/124; B41M 5/15; G01L 1/247; G01L 1/24; G03C 1/685
See application file for complete search history.

(56) References Cited

U.S. PATENT DOCUMENTS 7,049,152 B2 * 5/2006 Stevens .................. B82Y 10/00
424/422
7,242,443 B2 7/2007 Sage et al.
(Continued)

FOREIGN PATENT DOCUMENTS

CN 102643639 8/2012
CN 104880820 9/2015
(Continued)

OTHER PUBLICATIONS

WPIDS AN 2013-R64001, 201371.
(Continued)

*Primary Examiner* — Alvin J Stewart
(74) *Attorney, Agent, or Firm* — Lewis Kohn & Walker LLP; David M. Kohn

(57) ABSTRACT

A medical product which contains a mechanophore, and the use of a mechanophore for producing a medical product.

10 Claims, 8 Drawing Sheets

(51) Int. Cl.
*A61L 29/14* (2006.01)
*A61L 31/08* (2006.01)
*A61L 31/14* (2006.01)
*A61B 17/02* (2006.01)
*A61F 2/30* (2006.01)
*A61B 90/00* (2016.01)
*A61F 2/32* (2006.01)
*A61F 2/38* (2006.01)
*A61F 2/44* (2006.01)

(52) U.S. Cl.
CPC ......... *A61B 2090/0809* (2016.02); *A61F 2/32* (2013.01); *A61F 2/38* (2013.01); *A61F 2/442* (2013.01); *A61L 2400/00* (2013.01); *A61L 2420/06* (2013.01)

(56) References Cited

U.S. PATENT DOCUMENTS

| | | | |
|---|---|---|---|
| 8,236,914 B2 | 8/2012 | Potisek et al. | |
| 8,815,771 B2* | 8/2014 | Chopra | C08G 18/671 503/201 |
| 9,133,362 B2* | 9/2015 | Hickenboth | G01L 1/24 |
| 9,364,308 B2* | 6/2016 | Khamis | A61F 2/0045 |
| 9,675,561 B2* | 6/2017 | Bencherif | A61K 9/7007 |
| 9,918,818 B2* | 3/2018 | Khamis | A61F 2/0045 |
| 10,045,947 B2* | 8/2018 | Bencherif | A61K 39/0011 |
| 2003/0216732 A1* | 11/2003 | Truckai | A61B 18/14 606/49 |
| 2004/0064191 A1 | 4/2004 | Wasielewski | |
| 2007/0005145 A1 | 1/2007 | Banks et al. | |
| 2008/0074643 A1* | 3/2008 | Chen | G01L 1/24 356/32 |
| 2009/0121121 A1 | 5/2009 | Dunleavy et al. | |
| 2010/0206088 A1* | 8/2010 | Potisek | G01L 1/24 73/762 |
| 2010/0249658 A1 | 9/2010 | Sherman et al. | |
| 2012/0101515 A1* | 4/2012 | Barbod | A61M 25/104 606/194 |
| 2013/0018219 A1* | 1/2013 | Khamis | A61F 2/0045 600/30 |
| 2014/0013864 A1* | 1/2014 | Hickenboth | C09D 175/04 73/862.624 |
| 2014/0069202 A1 | 3/2014 | Fisk | |
| 2014/0112990 A1* | 4/2014 | Bencherif | A61K 39/0011 424/486 |
| 2014/0303739 A1 | 10/2014 | Mentink et al. | |
| 2017/0225395 A1* | 8/2017 | Boydston | B33Y 70/00 |
| 2017/0354792 A1* | 12/2017 | Ward | A61M 5/5086 |
| 2019/0105652 A1* | 4/2019 | Leslie | G01N 33/5302 |

FOREIGN PATENT DOCUMENTS

| | | |
|---|---|---|
| DE | 20320501 | 11/2004 |
| DE | 102013005874 | 10/2014 |
| WO | 2006105290 | 10/2006 |
| WO | 2012054140 | 4/2012 |
| WO | 20130158379 | 10/2013 |
| WO | 2016022661 | 2/2016 |

OTHER PUBLICATIONS

Ying Jian: "An outlook review: Mechanochromic materials and their potential for biological and healthcare applications" (2014) Materials and Science Engineering C 45:682-689.

Beiermann et al. "Role of Mechanophore Orientation in Mechanochemical Reactions" (2012) ACS Macro Letter 1:8236-8236.

Kim et al. "Mechanoactivation of Spiropyran Covalently Linked PMMA: Effect of Temperature, Strain Rate, and Deformation Mode" (2015) Macromolecules 48:1335-1342.

Beiermann et al. "Environmetal effects on mechanochemical activation of spiropyran in linear PMMA" (2011) J. Mater. Chem. 21:8443.

Kean et al. "Stress-Responsive Polymers Containing Cyclobutane Core Mechanophores: Reactivity and Mechanistic Insights" (2013) J. Am. Chem. Soc. 135:13598-13604.

Kingsbury et al. "Shear activation of mechanophore-crosslinked polymers" (2011) J. Mater. Chem. 21:8381-8388.

Brown and Craig "Molecular engineering of mechanophore activity for stress-responsive polymeric materials" (2015) Chem. Sci. 6:2158.

* cited by examiner

MECHANOPHORIC MEDICAL PRODUCT

This application is a United States National Stage Application claiming the benefit of priority under 35 U.S.C. 371 from International Patent Application No. PCT/EP2016/068540 filed Aug. 3, 2016, which claims the benefit of priority from German Patent Application Serial No. DE 102016203287.9 filed Feb. 29, 2016 and German Patent Application Serial No. DE 102015215112.3 filed Aug. 7, 2015, the entire contents of which are herein incorporated by reference.

FIELD OF USE AND PRIOR ART

The invention relates to a medical product which contains a mechanophore, and the use of a mechanophore for producing a medical product.

Polymers are almost ubiquitous nowadays: from packaging to special products in medical engineering. The polymers are thus exposed to stresses which can lead to damage to the polymer structure and consequently to material and product failure. The detection and location of material or product zones which are exposed to particularly high stresses through use is therefore of especial importance.

A method for the detection of material damage is known from WO 2006/105290 A2. The PCT laid-open specification proposes the use of colored substances which are integrated in a matrix in the form of capsules. Initially the color of the substances is not visible. Only through damage to the capsules are the colored substances released.

From WO 2007/003883 A1 the use of electromagnetic fibers which on damage can acquire inter alia luminescent properties is known.

A further approach consists in the use of so-called triboluminescent materials. These are materials which under severe mechanical stress display "cold light emission". Appropriate materials are for example known from U.S. Pat. No. 7,242,443 B2.

Mechanophore-containing polymers and mechanophore-containing compositions are known from WO 2009/018111 A1 and US 2014/0013864 A1. A mechanophore is understood to be a compound which under stress undergoes a chemically and/or physically detectable structural change, such as for example color change.

Mechanophore-containing polymers are also described in the non-patent literature: Beiermann et al.: "Role of Mechanophore Orientation in Mechanochemical Reactions" ACS Macro Lett. 2012, 1, 163-166; Kim et al.: "Mechanoactivation of Spiropyran Covalently Linked PMMA: Effect of Temperature, Strain Rate, and Deformation Mode", Macromolecules 2015, 48, 1335-1342; Beiermann et al.: "Environmental Effects on Mechanochemical Activation of Spiropyran in Linear PMMA" J. Mater. Chem., 2011, 21, 8443-8447; Kean et al.: "Stress-Responsive Polymers Containing Cyclobutane Core Mechanophores: Reactivity and Mechanistic Insights" J. Am. Chem. Soc. 2013, 135, 13598-13604; Kingsbury et al.: "Shear Activation of Mechanophore-Crosslinked Polymers" J. Mater. Chem., 2011 21, 8381-8388 and Brown and Craig: "Molecular Engineering of Mechanophore Activity for Stress-Responsive Polymeric Materials" Chem. Sci., 2015, 6, 2158-2165.

The detection of material or product failure is also of particular importance in the field of medical engineering. This applies particularly in the field of arthroplasty, i.e. for surgical operations which are intended to safeguard or restore the joint functions. Thus in the choice and positioning of an implant suitable in this respect, the ligament situation of the joints and the load distribution must constantly be taken into account.

For example, in the implementation of a total knee arthroplasty (TKA) the load must not be unequally distributed onto the medial and lateral compartment of the joint. Further, care must be taken that the ligament tension is not too low. On the other hand, however, the ligament tension must not be too great, in order to avoid a luxation, increased wear and restricted mobility. The operator must therefore select an appropriate implant position and a suitable sliding surface height.

A similar problem arises in the implementation of a total hip arthroplasty (THA). Here too, the ligament tension at the joint must be as optimally as possible adjusted on the basis of different implant variants and head/neck lengths. The assessment of a correct ligament tension and above all a uniform load distribution is a major challenge in this case also.

Until now, the assessment of the ligament tension is as a rule performed by the doctor by touch. During this, sample implant repositioning is undertaken in order to assess the joint stability. A disadvantage is that this is an exclusively subjective assessment of the ligament tension.

For knee arthroplasty, an electronic system solution can by now also be enlisted which enables in particular an assessment of the pressure distribution of the medial and lateral compartment. A disadvantage is that such system solutions require considerable investment expenditure.

PROBLEM AND SOLUTION

The present invention is therefore based on the problem of providing a medical product which allows as reliable and in particular objective as possible an assessment, preferably intraoperative assessment of forces arising in the body of a human or animal patient and in particular of force distributions in the human or animal body.

This problem is solved according to the invention by a medical product containing a mechanophore and by the use of a mechanophore for producing a medical product. Preferred embodiments are defined in the dependent claims. The wording of all claims is herewith by reference made part of the content of the description.

According to a first aspect, the invention relates to a medical product which contains a mechanophore.

In the sense of the present invention, the expression "mechanophore" should be understood to mean a compound according to the definition mentioned at the start, i.e. a compound which under stress undergoes a chemically and/or physically detectable structural change.

In the sense of the present invention, the expression "stress" should be understood to mean preferably a mechanical stress, in particular a tensile, compressive and/or shear stress.

Through the detectable structural change of the mechanophore under stress, it is possible to register and assess forces and in particular force distributions which act on the medical product and/or a treatment site in the body of a human or animal patient which is to be treated with the medical product. An assessment of such forces or force distributions can for example be made with a 3D microscope or an endoscope. In particular, an assessment of deformations of the medical product can be made in an automated manner by digital image processing.

The medical product according to the invention above all enables an intraoperative assessment of such forces or force distributions, especially in the implementation of implant operations. This is advantageous above all in the implementation of arthroplasty operations, where for the avoidance of ligament and/or tendon damage an exact as possible load indication and an exact as possible display of the load distribution, especially in artificial joints, are necessary. The medical product according to the invention thus contributes to a significant improvement in the medical treatment outcome, preferably implantation outcome, and to a reduced revision rate, particularly in the arthroplasty field.

In a preferred embodiment, the mechanophore is a component of a coating of the medical product or contained in a coating of the medical product. In other words, according to a preferred embodiment the mechanophore is a component of a layer of the medical product or contained in a layer of the medical product. The coating or layer is preferably formed on the surface (external surface) of the medical product.

In a preferred embodiment, the mechanophore is a component of a mixture or composition of the medical product.

In a further embodiment, the mixture or composition is a coating of the medical product. In other words, according to a further embodiment the mixture or composition forms a layer of the medical product. The coating or layer is preferably formed on the surface (external surface) of the medical product.

In an alternative embodiment, the mixture or composition is a bulk material of the medical product. In other words, the medical product according to an alternative embodiment consists of the mixture or composition.

In a further embodiment, the medical product, in particular the coating or the mixture or composition, further contains a polymer.

The polymer is preferably selected from the group comprising or consisting of polyolefins, polyethylene (PE), ultra-high molecular weight polyethylene (UHMWPE), polyvinyl chloride (PVC), polyvinylidene chloride, polyvinyl fluoride, polyvinylidene fluoride, polytetrafluorethylene (PTFE), polystyrene, polyvinyl alcohol (PVA), polyacrylic acid or polyacrylate, polymethacrylic acid or polymethacrylate, polymethylmethacrylic acid or polymethyl methacrylate, polydimethylsiloxane, polyoxymethylene (POM), polyoxyethylene, polyurethane, amorphous polymers, elastomers, thermoplastic elastomers, polypropylene, polytetrafluoropropylene, polyhexafluoropropylene, polyethylene glycol, polypropylene glycol, polyester, polyethylene terephthalic acid or polyethylene terephthalate, polypropylene terephthalic acid or polypropylene terephthalate, polybutylene terephthalic acid or polybutylene terephthalate, polyhydroxyalkanoic acids or polyhydroxyalkanoates, polylactic acid or polylactide, polyglycolic acid or polyglycolate, polyhydroxybutyric acid or polyhydroxybutyrate, poly-3-hydroxybutyric acid or poly-3-hydroxybutyrate, poly-4-hydroxybutyric acid or poly-4-hydroxybutyrate, polytrimethylene carbonate, poly-ε-caprolactone, poly-para-dioxanone, copolymers, in particular di- or terpolymers, and mixtures, in particular blends, thereof.

In a further embodiment, the mechanophore is covalently linked to the medical product, in particular polymer.

In particular, the mechanophore can be integrated covalently into the main chain (molecular backbone) of the polymer and/or covalently into a side chain of the polymer and/or form a side chain of the polymer.

Furthermore, molecules of the polymer can be crosslinked with one another via the mechanophore.

According to an alternative embodiment, the mechanophore is not covalently linked to the medical product, in particular polymer.

In a preferred embodiment, under stress the mechanophore undergoes a visible structural change. In this manner, the forces to be assessed can be visualized.

Particularly preferably, the mechanophore is a mechanochromic compound, i.e. a compound which under stress undergoes a color-producing or color-changing, in particular color tone, color saturation and/or color brightness-changing structural change. As a result, it is possible, through the occurrence of colorations or color changes, in particular color tone, color saturation and/or color brightness changes, to register and to assess forces and in particular force distributions.

The structural change is preferably accompanied by ring opening of the mechanophore.

According to the invention, it can moreover be preferred that the structural change of the mechanophore is reversible, in particular under the action of light, preferably UV light. In this manner, multiple use of the medical product is possible.

In a further embodiment, the mechanophore is selected from the group comprising or consisting of pyran compounds, oxazine compounds, fulgide compounds, fulgimide compounds, dimeric lactone compounds, dimeric imidazole compounds, oxicam compounds, piroxicam, indanedione compounds, 2,2'-bis[4-dimethylamino)phenyl]-1,3-indanedione, bicyclo compounds and mixtures thereof.

The pyran compounds can be selected from the group comprising or consisting of naphthopyran compounds, naphtho[1,2-b]pyran compounds, naphtho[2,1-b]pyran compounds, indeno-condensed naphthopyran compounds, heterocyclic-condensed naphthopyran compounds, spiro-9-fluoreno[1,2-b]pyran compounds, phenanthropyran compounds, quinolinepyran compounds, fluoroanthenopyran compounds, spiropyran compounds, spiro[benzindoline] naphthopyran compounds, spiro-(indoline)benzopyran compounds, spiro(indoline)naphtho-pyran compounds, spiro(indoline)quinolinepyran compounds, spiro(indoline)pyran compounds and mixtures thereof.

The pyran compounds can in particular be selected from the group comprising or consisting of 12-ethoxy-3-(2,4-dimethoxyphenyl)-3-(4-methoxyphenyl)-3H-benzo[H] pyrano[3,2-c]quinoline, 12-ethoxy-3-(2-fluorophenyl)-3-(4-methoxy)-3H-benzo[H]pyrano[3,2-c]-quinoline, 12-ethoxy-3,3-diphenyl-3H-benzo[H]pyrano-[3,2-c]quinoline, 2-(2,4-dimethoxyphenyl)-5-ethoxy-9-methoxy-2-(4-methoxyphenyl)-2H-pyrano[3,2-c]quinoline, 2-(4-(3-dimethylaminopropyl)methylaminophenyl)-2-phenyl-5-methoxycarbonyl-6-methyl-9-methoxy-2H-naphtho-[1,2-b] pyran, 2-(4-bis(3-dimethylaminopropyl)-aminophenyl)-2-phenyl-5-methoxycarbonyl-6-methyl-9-methoxy-2H-naphtho[1,2-b]pyran, 2-(4-methoxyphenyl)-2-(4-morpholinophenyl)-5-hydroxy-6-carboethoxy-2H-naphtho [1,2-b]pyran, 2-(4-methoxyphenyl)-2-phenyl-5-methoxycarbonyl-8,9-dimethoxy-2H-naphtho[1,2-b]pyran, 2-(4-methoxyphenyl)-2-phenyl-5-morpholino-6-carbomethoxy-9-methoxy-2H-naphtho[1,2-b]pyran, 2-(4-methoxyphenyl)-2-phenyl-5-morpholino-6-carbomethoxy-9-methyl-2H-naphtho[1,2-b]pyran, 2,2,5-triphenyl-6-carboethoxy-2H-naphtho[1,2-b]pyran, 2,2,7,7-tetraphenyl-4-oxo-2,3,4,7-tetrahydro-1H-[1,3]oxazino-[5',4':3,4] naphtho[1,2-b]pyran, 2,2,7,7-tetraphenyl-4-oxo-2,3,4,7-tetrahydro-1H-pyrimidino[5',4':3,4]naphtho-[1,2-b]pyran, 2,2-di(4-methoxyphenyl)-5-methoxy-carbonyl-6-(3,4-dimethoxyphenyl)-8,9-dimethoxy-2H-naphtho[1,2-b]pyran, 2,2-di(4-methoxyphenyl)-5-methoxy-carbonyl-6-methyl-8,9-dimethoxy-2H-naphtho[1,2-b]pyran, 2,2-di(4-methoxyphenyl)-5-methoxycarbonyl-6-phenyl-8,9- dimethoxy-2H-naphtho[1,2-b]pyran, 2,2-di(4-methoxyphenyl)-5-methoxycarbonyl-6-phenyl-8-morpholino-9-methoxy-2H-naphtho[1,2-b]pyran, 2,2-di(4-methoxyphenyl)-5-methoxycarbonyl-6-phenyl-8-piperidino-9-methoxy-2H-naphtho[1,2-b]pyran, 2,2-di(4-methoxyphenyl)-5-methoxycarbonyl-6-phenyl-9,10-dihydro-2H-[1,4]dioxino[2',3': 8,9]naphtho[1,2-b]pyran, 2,2-di-(4-methoxyphenyl)-5-methoxycarbonyl-8,9-dimethoxy-2H-naphtho[1,2-b]pyran, 2,2-diphenyl-5-hydroxy-6-carbomethoxy-9-methoxy-2H-naphtho[1,2-b]pyran, 2,2-diphenyl-5-methoxycarbonyl-6-(3,4-dimethoxyphenyl)-8,9-dimethoxy-2H-naphtho[1,2-b]pyran, 2,2-diphenyl-5-methoxycarbonyl-6-phenyl-2H-[1,3]dioxolo[4',5': 8,9]-naphtho[1,2-b]pyran, 2,2-diphenyl-5-methoxycarbonyl-8,9-dimethoxy-2H-naphtho[1,2-b]pyran, 2,2-diphenyl-6-methyl-5,6-dihydro-2H-pyrano[3,2-c]quinoline-5-on, 2,2-phenyl-5-hydroxy-6-carboethoxy-2H-naphtho[1,2-b]pyran, 2,2-phenyl-5-hydroxy-6-morpholinocarbonyl-2H-naphtho-[1,2-b]pyran, 2,2-phenyl-5-methoxy-6-carboethoxy-2H-naphtho[1,2-b]pyran, 2,2-phenyl-5-morpholino-6-carboethoxy-2H-naphtho[1,2-b]pyran, 2,7,7-triphenyl-4-oxo-4,7-dihydro[1,3]oxazino[5',6:3,4]naphtho[1,2-b]-pyran, 2,7,7-triphenyl-4-oxo-4H-7H-[1,3]dioxino-[5',4':3,4]naphtho[1,2-b]pyran, 2-phenyl-7-(4-methoxy-phenyl)-7-(4-morpholinophenyl)-4-oxo-4,7-dihydro[1,3]-oxazino[5',6:3,4]naphtha[1,2-b]pyran, 2-phenyl-7,7-di-(4-methoxyphenyl)-4-oxo-4,7-dihydro[1,3]oxazino-[5',6:3,4]naphtha[1,2-b]pyran, 2-propyl-7,7-di(4-methoxyphenyl)-4-oxo-4,7-dihydro[1,3]oxazino[5', 6:3,4]-naphtha[1,2-b]pyran, 3-(4-morpholinophenyl)-3-phenyl-6,11-difluoro-13,13-dimethyl-3H, 13H-indeno-[2',3':3,4]-naphtho[1,2-b]pyran, 3-(2-ethoxy carbonylethyl)-7,7-diphenyl-2,4dioxo-2,3,4,7-tetrahydro[1,3]oxazino-[5',6':3,4]naphtho[1,2-b]pyran, 3-(2-methacryloyloxy-ethyl)-7,7-diphenyl-2,4-dioxo-2,3,4,7-tetrahydro[1,3]-oxazino[5',6':3,4]naphtho[1,2-b]pyran, 3-(4-bis(3-dimethylaminopropyl)aminophenyl)3H-naphtho[2,11-b]pyran, 3-(4-fluorophenyl)-3-(4-(2-methylpiperidino)phenyl)-13,13-dimethyl-3H,13H-indeno[2',3':3,4]naphtho[1,2-b]pyran, 3-(4-fluorophenyl)-3-(4-(N,N-diethylamino)-phenyl)-13,13-dimethyl-3H, 13H-indeno[2',3':3,4]naphtho-[1,2-b]pyran, 3-(4-fluorophenyl)-3-(4-methoxyphenyl)-6,11-dichloro-13,13-dimethyl-3H, 13H-indeno[2',3':3,4]-naphtho[1,2-b]pyran, 3-(4-fluorophenyl)-3-(4-methoxy-phenyl)-6,11-difluoro-13,13-dimethyl-3H, 13H-indeno-[2',3':3,4]naphtho[1,2-b]pyran, 3-(4-fluorophenyl)-3-(4-methoxyphenyl)-6-methoxy-7-(4-(2-methacryloxyethyl)-carbamyloxypiperidin-1-yl)-13,13-dimethyl-3H, 13H-indeno[2',3':3,4]naphtho[1,2-b]pyran, 3-(4-fluoro-phenyl)-3-(4-morpholinophenyl)-13,13-dimethyl-3H, 13H-indeno[2',3':3,4]naphtho[1,2-b]pyran, 3-(4-fluoro-phenyl)-3-(4-morpholinophenyl)-6,11-difluoro-13,13-dimethyl-3H, 13H-indeno[2',3':3,4]naphtho[1,2-b]pyran, 3-(4-fluorophenyl)-3-(4-morpholinophenyl)-6-methoxy-7-(4-(2-methacryloxyethyl)carbamyloxypiperidin-1-yl)-13,13-dimethyl-3H, 13H-indeno[2',3':3,4]naphtho[1,2-b]-pyran, 3-(4-fluorophenyl)-3-(4-piperazinophenyl)-13,13-dimethyl-3H, 13H-indeno[2',3': 3,4]naphtho[1,2-b]pyran, 3-(4-fluorophenyl)-3-(4-piperidinophenyl)-13,13-dimethyl-3H,13H-indeno[2',3':3,4]naphtho[1,2-b]pyran, 3-(4-fluoro-phenyl)-3-(4-piperidinophenyl)-6,11-difluoro-13,13-dimethyl-3H,13H-indeno[2',3':3,4]-naphtho[1,2-b]pyran, 3-(4-fluorophenyl)-3-(4-pyrrolidinophenyl)-13,13-dimethyl-3H, 13H-indeno-[2',3': 3,4]naphtho[1,2-b]pyran, 3-(4-fluoro-phenyl)-3-ferrocenyl-13,13-dimethyl-3H,13H-indeno[2',3': 3,4]-naphtho[1,2-b]pyran, 3-(4-fluorophenyl)-3-ferrocenyl-6,7-dimethoxy-11-phenyl-13,13-dimethyl-3H, 13H-indeno-[2',3': 3,4]naphtho[1,2-b]pyran, 3-(4-fluorophenyl)-3-ferrocenyl-6,7-dimethoxy-13,13-dimethyl-3H, 13H-indeno-[2', 3': 3,4]naphtho[1,2-b]pyran, 3-(4-fluorophenyl)-3-ferrocenyl-6,7-dimethoxy-13-ethyl-13-hydroxy-3H, 13H-indeno[2',3': 3,4]naphtho[1,2-b]pyran, 3-(4-fluoro-phenyl)-3-ferrocenyl-6-morpholino-7-methoxy-13-ethyl-13-hydroxy-3H, 13H-indeno[2',3':3,4]naphtho[1,2-b]pyran, 3-(4-fluorophenyl)-3-phenyl-13,13-dimethyl-3H, 13H-indeno[2',3':3,4]naphtho[1,2-b]pyran, 3-(4-methoxy-phenyl)-3-(4-morpholinophenyl)-6,7-dimethoxy-13-ethyl-13-methoxy-3H,13H-indeno[2,1-f]naphtho[1,2-b]pyran, 3-(4-methoxyphenyl)-3-(2,3-dihydrobenzofur-5-yl)-13-acetoxy-6,11-dimethoxy-13-methyl-indeno[2,1-f]naphtho-[1,2-b]pyran, 3-(4-methoxyphenyl)-3-(2,3-dihydrobenzo-fur-5-yl)-13-hydroxy-13-methyl-indeno[2,1-f]naphtho-[1,2-b]pyran, 3-(4-methoxyphenyl)-3-(3,4-dimethoxyphenyl)-6,11-dimethyl-13,13-dipropyl-indeno-[2,1-f]naphtho[1,2-b]pyran, 3-(4-methoxyphenyl)-3-(3-methyl-4-methoxyphenyl)-3-hydroxy-indeno[2,1-f]-naphtho[1,2-b]pyran, 3-(4-methoxyphenyl)-3-(4-dimethyl-aminophenyl)-6,7-dimethoxy-13,13-dimethyl-3H, 13H-indeno[2,1-f]naphtho[1,2-b]pyran, 3-(4-methoxyphenyl)-3-(4-morpholinophenyl)-16-(ethoxycarbonyl)methyl-16-hydroxy-3,16-di[H]-benzofuro[2',3':7,8]indeno-[2',3': 3,4]naphtho[1.2-b]pyran, 3-(4-methoxyphenyl)-3-(4-morpholinophenyl)-6,11-difluoro-13,13-dimethyl-3H,13H-indeno[2',3':3,4]naphtho[1,2-b]pyran, 3-(4-methoxyphenyl)-3-(4-morpholinophenyl)-6,7,10,11-tetra-methoxy-13-hydroxy-13-butyl-3H,13H-indeno[2,1-f]-naphtho[1,2-b]pyran, 3-(4-methoxyphenyl)-3-(4-morpholino-phenyl)-6,7,10,11-tetramethoxy-13-hydroxy-13-ethyl-3H, 13H-indeno[2,1-f]naphtho[1,2-b]pyran, 3-(4-methoxyphenyl)-3-(4-morpholinophenyl)-6,7-dimethoxy-13,13-dimethyl-3H, 13H-indeno[2,1-f]naphtho[1,2-b]pyran, 3-(4-methoxyphenyl)-3-(4-morpholinophenyl)-6,7-dimethoxy-13-hydroxy-13-ethyl-3H, 13H-indeno[2,1 f]-naphtho[1,2-b]pyran, 3-(4-methoxyphenyl)-3-(4-morpholinophenyl)-6,7-dimethoxy-13-hydroxy-13-methyl-3H, 13H-indeno[2,1-f]naphtho[1,2-b]pyran, 3-(4-methoxy-phenyl)-3-(4-morpholinophenyl)-6,7-dimethoxy-13-methoxy-13-methyl-3H, 13H-indeno[2,1-f]naphtho[1,2-b]-pyran, 3-(4-methoxyphenyl)-3-(4-morpholinophenyl)-6,7-dimethoxy-13-phenyl-3H,13H-indeno[2,1-f]naphtho[1,2-b]-pyran, 3-(4-methoxyphenyl)-3-(5-methylthiophen-2-yl)-6,11-dichloro-13,13-dimethyl-3H, 13H-indeno[2',3':3,4]naphtho[1,2-b]pyran, 3-(4-methoxyphenyl)-3,9-diphenyl-3H-9H-indeno[3',2':3,4]naphtho[1,2-b]pyran, 3-(4-methoxyphenyl)-3-phenyl-6-bromo-13,13-dimethyl-3H, 13H-indeno [2',3': 3,4]naphtho[1,2-b]pyran, 3-(4-methoxy-phenyl)-3-phenyl-9-(3-methoxyphenyl)-11-methoxy-3H-9H-indeno[3',2':3,4]naphtho[1,2-b]pyran, 3-(4-methoxy-phenyl)-3-phenyl-9,9-dimethyl-11-methoxy-3H-9H-indeno[3',2':3,4]naphtho[1,2-b]pyran, 3-(4-methoxy-phenyl)-3-phenyl-9,9-dimethyl-3H-9H-benzo[4",5"]-indeno[3',2':3,4]naphtho[1,2-b]pyran, 3-(4-methoxy-phenyl)-3-phenyl-9,9-dimethyl-7,11-dimethoxy-3H-9H-indeno[3',2':3,4]naptho[1,2-b]pyran, 3-(4-methoxy-phenyl)-3-phenyl-9-methyl-11,13-dimethoxy-3H-9H-indeno-[3',2':3,4]naphtho[1,2-b]pyran, 3-(4-methoxyphenyl)-3-phenyl-9-methyl-11-methoxy-9-(3-methoxyphenyl)-3H-9H-indeno[3',2':3,4]naphtho[1,2-b]-pyran, 3-(4-methyl-phenyl)-3-(4-morpholinophenyl)-6,11-difluoro-13,13-dimethyl-3H, 13H-indeno[2',3':3,4]naphtho[1,2-b]pyran, 3-(4-morpholinophenyl)-3,9-diphenyl-3H-9H-indeno-[3',2':3,4]naphtho[1,2-b]pyran, 3-(4-morpholinophenyl)-3-phenyl-13,13-dimethyl-3H, 13H-indeno[2',3':3,4]-naphtho[1,2-b]pyran, 3-(4-morpholinophenyl)-3-phenyl-6,11-difluoro-13,13-dimethyl-3H, 13H-indeno[2',3':3,4]-naphtho[1,2-b]pyran, 3-(4-morpholinophenyl)-3-phenyl-6,7-dimethoxy-13-hydroxy-13-butyl-3H, 13H-indeno[2,1-f]naphtho[1,2-b]pyran, 3-(4-morpholinophenyl)-3-phenyl-6,7-dimethoxy-13-hydroxy-13-ethyl-3H,13H-indeno[2,1-f]naphtho[1,2-b]pyran, 3-(4-morpholinophenyl)-3-phenyl-6-bromo-13,13-dimethyl-3H, 13H-indeno[2',3':3,4]naphtho-[1,2-b]pyran, 3-(4-morpholinophenyl)-3-phenyl-9,9-dimethyl-7,11-dimethoxy-3H-9H-indeno[3',2':3,4]naphtho-[1,2-b]pyran, 3,3,9-triphenyl-3H-9H-indeno[3',2':3,4]-naphtho[1,2-b]pyran, 3,3-di(4-methoxyphenyl)-6,11-dimethyl-13-(1-methylethyl)-13-hydroxy-indeno[2,1-f]-naphtho[1,2-b]pyran, 3,3-di(4-fluorophenyl)-6,11-di(methoxycarbonyl)-13,13-dimethyl-3H, 13H-indeno-[2',3':3,4]naphtho[1,2-b]pyran, 3,3-di(4-fluorophenyl)-6,11-dichloro-13,13-dimethyl-3H,13H-indeno[2',3':3,4]-naphtho[1,2-b]pyran, 3,3-di(4-fluorophenyl)-6,11-dicyano-13,13-dimethyl-3H, 13H-indeno[2',3':3,4]naphtho-[1,2-b]pyran, 3,3-di(4-fluorophenyl)-6,11-difluoro-13,13-dimethyl-3H, 13H-indeno[2',3':3,4]naphtho[1,2-b]-pyran, 3,3-di(4-fluorophenyl)-6-cyano-13,13-dimethyl-3H, 13H-indeno[2',3':3,4]naphtho[1,2-b]pyran, 3,3-di(4-fluorophenyl)-6-methoxycarbonyl-13,13-dimethyl-3H, 13H-indeno[2',3':3,4]naphtho[1,2-b]pyran, 3,3-di(4-methoxy-phenyl)-13-hydroxy-13-methyl-indeno[2,1-f]naphtho[1,2-b]pyran, 3,3-di(4-methoxyphenyl)-16-(ethoxycarbonyl)-methyl-16-hydroxy-3,16-di[H]benzofuro[2',3':7,8]indeno-[2',3':3,4]naphtho[1,2-b)pyran, 3,3-di(4-methoxy-phenyl)-16-hydroxy-16-ethyl-16H-benzofuro[2',3': 7,8]-indeno[2',3':3,4]naphtho[1,2-b]pyran, 3,3-di(4-methoxy-phenyl)-16-hydroxy-16-ethyl-16H-benzofuro-[2'',3'': 6',7']indeno[3',2':4,3]naphtho[1,2-b]pyran, 3,3-di(4-methoxyphenyl)-16-hydroxy-16H-benzofuro-[2'',3'': 6',7']indeno[3',2':4,3]naphtho[1,2-b]pyran, 3,3-di(4-methoxyphenyl)-6,11-dimethyl-13-butyl-13-hydroxy-indeno[2,1-f]naphtho[1,2-b]pyran, 3,3-di(4-methoxyphenyl)-6,11-di(methoxycarbonyl)-13,13-dimethyl-3H, 13H-indeno[2',3':3,4]naphtho[1,2-b]pyran, 3,3-di(4-methoxyphenyl)-6,11-dichloro-13,13-dimethyl-3H,13H-indeno[2',3':3,4]naphtho[1,2-b]pyran, 3,3-di(4-methoxy-phenyl)-6,11-difluoro-13,13-dimethyl-3H, 13H-indeno-[2',3':3,4]naphtho[1,2-b]pyran, 3,3-di(4-methoxy-phenyl)-6,11-dimethyl-13-methoxyindeno[2,1-f]naphtho-[1,2-b]pyran, 3,3-di(4-methoxyphenyl)-6,7,10,11-tetra-methoxy-13,13-diethyl-3H, 13H-indeno[2,1-f]naphtho[1,2-b]pyran, 3,3-di(4-methoxyphenyl)-6,7,10,11-tetramethoxy-13,13-dimethyl-3H, 13H-indeno[2,1-f]-naphtho[1,2-b]pyran, 3,3-di(4-methoxyphenyl)-6,7,10,11-tetramethoxy-13-hydroxy-13-ethyl-3H,13H-indeno[2,1-f]-naphtho[1,2-b]pyran, 3,3-di(4-methoxyphenyl)-6,7,8-trimethoxy-13-phenyl-3H, 13H-indeno[2,1-f]naphtho[1,2-b]pyran, 3,3-di(4-methoxyphenyl)-6,7-dimethoxy-13,13-dimethyl-3H, 13H-indeno[2,1-f]naphtho[1,2-b]pyran, 3,3-di(4-methoxyphenyl)-6,7-dimethoxy-13-hydroxy-13-butyl-3H, 13H-indeno[2,1-f]naphtho[1,2-b]pyran, 3,3-di(4-methoxyphenyl)-6,7-dimethoxy-13-hydroxy-13-ethyl-3H, 13H-indeno[2,1-f]naphtho[1,2-b]pyran, 3,3-di(4-methoxy-phenyl)-6,7-dimethoxy-13-phenyl-3H,13H-indeno-[2,1-f]naphtho[1,2-b]pyran, 3,3-di(4-methoxyphenyl)-6-methoxy-7-(3-(2-methacryloxyethyl)carbamyloxymethylene-piperidin-1-yl)-13,13-dimethyl-3H, 13H-indeno-[2',3':3,4]naphtho[1,2-b]pyran, 3,3-di(4-methoxy)-6-methyl-11-fluoro-13,13-diethoxy-indeno[2,1-f]naphtho[1,2-b]pyran, 3,3-di(4-methoxyphenyl)-9-(3-methoxyphenyl)-11-methoxy-3H-9H-indeno[3',2':3,4]-naphtho[1,2-b]pyran, 3,3-di(4-methoxyphenyl)-9,9-dimethyl-11-fluoro-3H-9H-indeno[3',2':3,4]naphtho[1,2-b]pyran, 3,3-di(4-methoxy-phenyl)-9,9-dimethyl-1-methoxy-3H-9H-indeno[3',2':3,4]-naphtho[1,2-b]pyran, 3,3-di(4-methoxyphenyl)-9,9-dimethyl-7,11-dimethoxy-3H-9H-indeno[3',2':3,4]naphtho[1,2-b]pyran, 3,3-di(4-methoxyphenyl)-9-methyl-11,13-dimethoxy-3H-9H-indeno-[3',2':3,4]naphtho[1,2-b]pyran, 3,3-di(4-methoxy-phenyl)-9-methyl-11-methoxy-3H-9H-indeno[3',2':3,4]-naphtho[1,2-b]pyran, 3,3-di(4-methoxy-phenyl)-9-methyl-11-methoxy-9-(3-methoxyphenyl)-3H-9H-indeno[3',2':3,4]-naphtho[1,2-b]pyran, 3,3-di(4-methoxyphenyl)-9-phenyl-3H-9H-indeno[3',2':3,4]naphtho[1,2-b]pyran, 3,3-diphenyl-13,13-dimethyl-3H, 13H-indeno[2',3':3,4]-naphtho[1,2-b]pyran, 3,3-diphenyl-6,11-dicyano-13,13-dimethyl-3H, 13H-indeno[2',3':3,4]naphtho[1,2-b]pyran, 3-hexyl-7,7-diphenyl-2,4-dioxo-2,3,4,7-tetrahydro[1,3]-oxazino[5',6':3,4]naphtho[1,2-b]pyran, 3-methyl-7,7-diphenyl-2,4-dioxo-2,3,4,7-tetrahydro[1,3]oxazino-[5',6':3,4]naphtho[1,2-b]pyran, 3-phenyl-3-(4-(2-(2-(2-(2-(2-(2-(2-(2-methacryloxyethoxy)ethoxy)ethoxy)-ethoxy)ethoxy)carbonylethyl)carboxyethoxy)phenyl)-6-methoxy-7-morpholino-13,13-dimethyl-3H, 13H-indeno-[2',3':3,4]naphtho[1,2-b]pyran, 3-phenyl-3-(4-(2-(2-(2-methacryloxyethyl)carbamyloxyethoxy)phenyl)-6,7-dimethoxy-13,13-dimethyl-3H, 13H-indeno[2',3':3,4]-naphtho[1,2-b]pyran, 3-phenyl-3-(4-(2-(2-methacryloxy-ethyl)carbamyloxyethoxy)phenyl)-6-methoxy-7-piperidino-13,13-dimethyl-3H, 13H-indeno[2',3':3,4]naphtho[1,2-b]-pyran, 3-phenyl-3-(4-(2-methacryloxyethyl)carbamyloxy-phenyl)-6,7-dimethoxy-13,13-dimethyl-3H, 13H-indeno-[2',3':3,4]naphtho[1,2-b]pyran, 3-phenyl-3-(4-(4-(2-(2-methacryloxyethyl)carbanlyloxyethyl)piperazin-1-yl)-phenyl)-13,13-dimethyl-3H,13H-indeno[2',3': 3,4]naphtho-[1,2-b]pyran, 3-phenyl-3-(4-(4-(2-methacryloxyethyl)-carbamylpiperazin-1-yl)phenyl)-6,11-dimethoxy-13,13-dimethyl-3H,13H-indeno[2',3':3,4]naphtho[1,2-b]pyran, 3-phenyl-3-(4-(4-phenylpiperazino)phenyl)-6-methoxy-7-(4-(2-methacryloxy ethyl)carbamyloxypiperidin-1-yl)-13,13-dimethyl-3H, 13H-indeno[2',3': 3,4]naphtho[1,2-b]pyran, 3-phenyl-3-(4-methoxyphenyl)-16-(ethoxycarbonyl)methyl-16-hydroxy-3.16-di[H]-benzofuro-[2'',3'': 6',7']indeno[3',2':4,3]naphtho[1,2-b]pyran, 3-phenyl-3-(4-methoxyphenyl)-6-methoxy-7-(3-(2-(2-(2-(2-(2-(2-(2-methacryloxyethoxy)ethoxy)ethoxy)-ethoxy)ethoxy)carbonylethyl)carboxymethylenepiperidin-1-yl)-13,13-dimethyl-3H, 13H-indeno[2',3':3,4]naphtho-[1,2-b]pyran, 3-phenyl-3-(4-methoxyphenyl)-6-methoxy-7-(4-(2-(2-(2-(2-(2-(2-methacryloxyethoxy)ethoxy)-ethoxy)ethoxy)ethoxy)carbonylpiperidin-1-yl)-13,13-dimethyl-3H, 13H-indeno-[2',3':3,4]naphtho[1,2-b]pyran, 3-phenyl-3-(4-methoxy-phenyl)-6-methoxy-7-(4-(2-methacryloxyethyl)carbamyl-piperazin-1-yl)-13,13-dimethyl-3H,13H-indeno-[2',3':3,4]naphtho[1,2-b]pyran, 3-phenyl-3-(4-morpholinophenyl)-16-(ethoxycarbonyl)methyl-16-hydroxy-3,16-di[H]benzofuro[2'',3'':6',7']indeno[3',2':4,3]-naphtho[1.2-b]pyran, 3-phenyl-3-(4-morpholino-phenyl)-6,7,10,11-tetramethoxy-13,13-dimethyl-3H, 13H-indeno-[2,1-f]naphtho[1,2-b]pyran, 3-phenyl-3-(4-morpholino-phenyl)-6-methoxy-7-(3-(2-(2-(2-(2-(2-(2-(2-methacryl-oxyethoxy)ethoxy)ethoxy)ethoxy)ethoxy)carbonyl-ethyl)carboxymethylenepiperidin-1-yl)-13,13-dimethyl-3H, 13H-indeno[2',3':3,4]naphtho[1,2-b]pyran, 3-phenyl-3-(4-morpholinophenyl)-6-methoxy-7-(3-(2-methacryl-oxyethyl)carbamyloxymethylenepiperidin-1-yl)-13,13-dimethyl-3H, 13H-indeno[2',3':3,4]naphtho[1,2-b]pyran, 3-phenyl-3-(4-morpholinophenyl)-6-methoxy-7-(4-(2-(2-(2-(2-(2-(2-(2-methacryloxyethoxy)ethoxy)ethoxy)-ethoxy)ethoxy)carbonylethyl)carboxypiperidin-1-yl)-13,13-dimethyl-3H, 13H-indeno[2',3':3,4]naphtho[1,2-b]pyran, 3-phenyl-3-(4-morpholinophenyl)-6-methoxy-7-(4-(2-methacryloxyethyl)carbamyloxypiperidin-1-yl)-13,13-dimethyl-3H, 13H- indeno[2',3':3,4]naphtho[1,2-b]pyran, 3-phenyl-3-(4-morpholinophenyl)-6-methoxy-7-(4-(2-methacryloxyethyl)carbamylpiperazin-1-yl)-13,13-dimethyl-3H, 13H-indeno[2',3':3,4]naphtho[1,2-b]pyran, 3-phenyl-3-(4-piperidinophenyl)-13,13-dimethyl-3H, 13H-indeno[2',3':3,4]naphtho[1,2-b]pyran, 3-phenyl-3-(4-piperidinophenyl)-6,11-dichloro-13,13-dimethyl-3H, 13H-indeno[2',3':3,4]naphtho[1,2-b]pyran, 3-phenyl-3-(4-piperidinophenyl)-6,11-difluoro-13,13-dimethyl-3H, 13H-indeno[2',3':3,4]naphtho[1,2-b]pyran, 3-phenyl-3-(4-piperidinophenyl)-6,11-difluoro-13,13-dimethyl-3H, 13H-indeno[2',3':3,4]naphtho[1,2-b]pyran, 3-phenyl-3-ferrocenyl-13,13-dimethyl-3H, 13H-indeno[2',3':3,4]-naphtho[1,2-b]pyran, 5-ethoxy-2-(2-fluorophenyl)-7-methoxy-2-(4-methoxyphenyl)-2H-pyrano[3,2-c]quinoline, 5-ethoxy-2-(2-fluorophenyl)-9-methoxy-2-(4-methoxy-phenyl)-2H-pyrano[3,2-c]quinoline, 5-ethoxy-2,2-diphenyl-2H-pyrano[3,2-c]quinoline, 5-ethoxy-3-(2-fluorophenyl)-3-(4-methoxy)-2H-[1,3]-dioxolo[4,5-g]-pyrano[3,2-c]quinoline, 5-ethoxy-7,9-dimethoxy-2,2-diphenyl-2H-pyrano[3,2-c]quinoline, 5-ethoxy-7-methoxy-2,2-diphenyl-2H-pyrano[3,2-c]quinoline, 5-ethoxy-9-fluoro-2,2-diphenyl-2H-pyrano[3,2-c]quinoline, 5-ethoxy-9-methoxy-2,2-diphenyl-2H-pyrano[3,2-c]-quinoline, 5-methoxy-2,2-diphenyl-2H-pyrano[3,2-c]-quinoline, 6-(4-methoxyphenyl)-8,9-dimethoxy-3-(2-fluorophenyl)-3-(4-methoxyphenyl)-3H-naphtho[2,1-b]-pyran, 6-(4-methoxyphenyl)-8,9-dimethoxy-3,3-diphenyl-3H-naphtho[2,1-b]pyran, 6-(4-methylphenyl)-3-(2-fluorophenyl)-3-(4-methoxyphenyl)-3H-naphtho[2,1-b]-pyran, 6-(4-methylphenyl)-3,3-diphenyl-3H-naphtho[2,1-b]pyran, 6-phenyl-8,9-dimethoxy-3-(2-fluorophenyl)-3-(4-methoxyphenyl)-3H-naphtho[2,1-b]pyran, 6-phenyl-8,9-dimethoxy-3,3-diphenyl-3H-naphtho[2,1-b]pyran, 7-(4-methoxyphenyl)-7-phenyl-2-pentyl-4-oxo-4H-7H-[1,3]-dioxino[5',4': 3,4]naphtho[1,2-b]pyran, 7,7-di(4-methoxyphenyl)-4-oxo-4H-7H-[1,3]dioxino[5',4':3,4]-naphtho[1,2-b]pyran, 7,7-diphenyl-1,2,4,7-tetrahydro-2,2-dimethylpyrano[3',4':3,4]naphtho[1,2-b]pyran, 7,7-diphenyl-2-(1-phenylethyl)-4-oxo-4H-7H-[1,3]dioxino-[5',4':3,4]naphtho[1,2-b]pyran, 7,7-diphenyl-2-(2-methylpropyl)-4-oxo-4H-7H-[1,3]dioxino[5',4':3,4]-naphtho[1,2-b]pyran, 7,7-diphenyl-2-ethyl-4-oxo-4H-7H-[1,3]dioxino[5',4': 3,4]naphtho[1,2-b]pyran, 7,7-diphenyl-2-pentyl-4-oxo-4H-7H-[1,3]dioxino[5',4': 3,4]-naphtho[1,2-b]pyran and 7,7-diphenyl-4-oxo-4H-7H-[1,3]dioxino[5',4':3,4]naphtho[1,2-b]pyran, 2,2-bis(4-methoxyphenyl)-5-(N-methylpyrrol-2-yl)-6-acetoxy-2H-naphtho[1.2-b]pyran, 2,2-bis(4-methoxyphenyl)-5-(2,4-dimethoxyphenyl)-6-acetoxy-2H-naphtho[1,2-b]pyran, 2,2-bis(4-methoxyphenyl)-5-phenylthio-6-hydroxy-2H-naphtho-[1,2-b]pyran, 2,2-bis(4-methoxyphenyl)-5-phenylthio-6-acetoxy-2H-naphtho[1,2-b]pyran, 2,2-bis(4-methoxy-phenyl)-5-chloro-6-acetoxy-2H-naphtho[1,2-b]pyran, 2,2-bis(4-methoxyphenyl)-5-methyl-6-acetoxy-2H-naphtho[1,2-b]pyran, 2,2'-spiroadamantylen-5-phenylthio-6-hydroxy-2H-naphtho[1,2-b]pyran, 2,2'-spiroadamantylen-5-phenyl-thio-6-acetoxy-2H-naphtho[1,2-b]pyran, 2,2'-spiroadamantylen-5-methyl-6-methoxy-2H-naphtho[1,2-b]-pyran, 2,2-bis(4-methoxyphenyl)-5-diphenylmethylol-6-hydroxy-2H-naphtho[1,2-b]pyran, 2,2-bis(4-methoxy-phenyl)-5-diphenylmethylol-6-methoxy-2H-naphtho[1,2-b]-pyran, 1,3-trimethylspiro[indoline-2,2'-[2H]-naphtho-[1,2-b]pyran], 1,3,3,5,6-pentamethylspiro[indoline-2,2'-[2H]-naphtho[1,2-b]pyran], 1,3-trimethyl-5-methoxyspiro[indoline-2,2'-[2H]-naphtho[1,2-b]pyran], 1,3-trimethyl-6'-chlorospiro[indoline-2,2'-[2H]-naphthol[1,2-b]pyran] and 1,3,3-trimethyl-6'-nitrospiro-[indoline-2,2'-[2H]-naphthol[1,2-b]pyran] and mixtures thereof.

The fulgide and the fulgimide compounds can in particular be selected from the group comprising or consisting of (E)-α-(1,2,5-trimethyl-3-pyrryl)-ethylidene(isopropylidene) succinic anhydride, (E)-α-(2,5-dimethyl-1-phenyl-3-pyrryl)ethylidene-(isopropylidene)succinic anhydride, (E)-α-(2,5-dimethyl-1-p-tolyl-3-pyrryl)ethylidene(isopropylidene)-succinic anhydride, (E)-α-(1,5-diphenyl-2-methyl-3-pyrryl)ethylidene(iso[propylidene)succinic anhydride and (E)-α-(2,5-dimethyl-1-phenyl-3-pyrryl)ethylidene-(dicyclopropylmethylene)succinic anhydride and mixtures thereof.

The diarylethene compounds can in particular be selected from the group comprising or consisting of 1,2-bis(2-(2-benzothiazolyl)-benzo[b]thien-3-yl)-perfluorocyclopentene and 1,2-bis-(2,5-bis-(2-benzothiazolyl)-thien-3-yl)perfluorocyclopentene and mixtures thereof. The oxazine compounds can be selected from the group comprising benzoxazine compounds, naphthoxazine compounds, spirooxazine compounds, spiro(indoline)naphthoxazine compounds, spiro-(indoline)pyridobenzoxazine compounds, spiro-(benzindoline)pyridobenzoxazine compounds, spiro-(benzindoline)naphthoxazine compounds, spiro-(indoline)benzoxazine compounds, spiro(indoline)-fluoranthenoxazine compounds, spiro(indoline)-quinoxazine compounds and mixtures thereof.

The dimeric lactone compound can for example be dibenzofuranone.

The dimeric imidazole compounds can for example be 2,4,5-triarylimidazole.

The bicyclo compounds can in particular be bicyclo [4.2.0]octane (BCO) or bicyclo[4.2.0]octane compounds (BCO compounds).

In a preferred embodiment, the mechanophore has the following formula I:

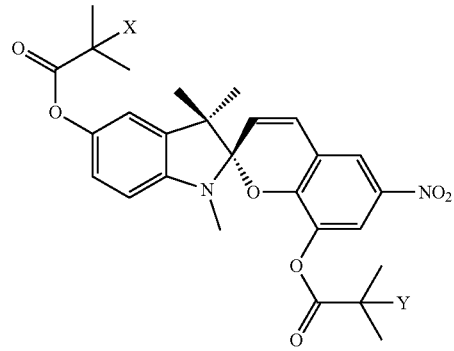

Formula I wherein X and Y can be the same or different and mutually independently mean an alkyl group, in particular methyl group (CH₃), a halogen atom, preferably bromine atom (Br) or chlorine atom (Cl), or a hydrogen (H).

The mechanophore according to formula I is convertible under stress into an acyclic compound according to formula II:

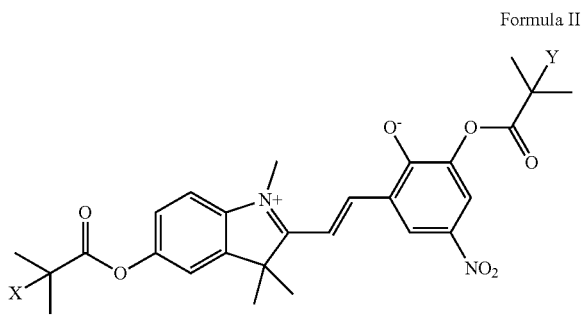

Formula II wherein X and Y can be the same or different and mutually independently mean an alkyl group, in particular methyl group ($CH_3$), a halogen atom, preferably bromine atom (Br) or chlorine atom (Cl), or a hydrogen (H).

The mechanophore according to formula I is colorless or yellowish, whereas the mechanophore according to formula II possesses a red or violet coloration and is strongly fluorescent. In this manner, forces acting on the medical product according to the invention can be visualized, in particular by fluorescence measurements.

In a further embodiment, the medical product contains additives. The additives can be selected from the group comprising or consisting of antiproliferative active substances, antimicrobial, in particular antibiotic, active substances, inflammation-inhibiting active substances, analgesic active substances, odor control active substances, disinfecting active substances, biological growth factors, radio-opaque substances and mixtures thereof.

The medical product is preferably an implant or implant part, in particular a human medical or surgical implant or implant part.

The implant or implant part can in principle be intended for permanent or only transient residence in the body of a human or animal patient. Correspondingly, the implant or implant part can be a permanent or temporary implant or implant part. For example, the implant or implant part can be intended to remain in a site merely for the duration of an infection treatment. The implant or implant part is preferably intended for use in the treatment of a joint defect, in particular knee or hip joint defect.

Preferably, the implant or implant part is intended for the implementation of an arthroplasty, in particular knee or hip arthroplasty operation.

In a further embodiment, the implant or implant part is intended for use in the measurement and/or assessment of the ligament and/or tendon tension in the body of a human or animal patient, preferably for use in the measurement and/or assessment of the ligament and/or tendon tension in human or animal joints.

According to a particularly preferable embodiment, the implant is a joint prosthesis.

The implant part is preferably a part of a joint prosthesis, preferably a head or head part, a socket or a socket part, an insert or an inlay, in particular cup inlay, or a sliding surface. In other words, the implant part is preferably a joint head or joint head part, a joint socket or a joint socket part, a joint insert or a joint inlay or a joint sliding surface.

Particularly preferably, the implant part is selected from the group comprising or consisting of hip joint head or hip joint head part, hip joint socket or hip joint socket part, hip joint insert or hip joint inlay, hip joint sliding surface, knee joint head or knee joint head part, knee joint socket or knee joint socket part, knee joint insert or knee joint inlay and knee joint sliding surface.

In a further embodiment, the aforementioned joint prosthesis is selected from the group comprising knee joint prosthesis, hip joint prosthesis, ankle joint prosthesis, shoulder joint prosthesis, mandibular joint prosthesis, elbow joint prosthesis, finger joint prosthesis and spinal facet prosthesis.

In a further embodiment, the implant is an artificial tibia or an artificial femur.

In a further embodiment, the implant or implant part is an implant for the spinal column, i.e. a so-called spinal implant, preferably an intervertebral implant or an implant part for the spinal column, i.e. a so-called spinal implant part, preferably an intervertebral implant part. An intervertebral implant is inserted into intervertebral spaces after the removal of an intervertebral disk.

In a further embodiment, the implant is a meniscus implant. The meniscus implant can be configured to replace a meniscus completely or only partially. Preferably, the meniscus implant has at least one articulation surface, in particular one or two articulation surfaces, for effecting an articulation with a femur (thigh bone) or at least one articulation surface, in particular one or two articulation surfaces, for effecting an articulation with a tibia (shin bone).

In a particularly preferable embodiment, the medical product, in particular the implant or implant part, is a so-called trial implant or trial implant part. In the sense of the present invention, the expression "trial implant" should be understood to mean an implant or instrument, preferably for use in the context of a surgical operation for joint replacement, for joint surface replacement or for intervertebral disk replacement. In its shape, the trial implant is modeled on a final implant, preferably one intended for the replacement of a joint, a joint surface or an intervertebral disk, or a final medical instrument. Accordingly, the expression "trial implant part" should be understood to mean a part of a trial implant.

By means of the trial implant, in particular the site of a final implant and the joint kinematics possible with this can be tested.

Furthermore, the trial implant can fulfil additional functions. Thus the trial implant for example can serve as a seating for further instruments or as a guidance instrument for further instruments. By means of a trial implant according to the invention, particularly advantageously for example the press fit with which implants are anchored cement-free on/in the bone can be checked. In this case, the trial implant can for example color up to a clearly defined color. If this color is not attained, this is an indication of too slight a press fit. If conversely another color is indicated, this can be regarded as an indication for too high a press fit.

In addition, the trial implant can be advantageous in the implementation of repositioning manoeuvers. Thus by means of an appropriately configured trial implant for all repositioning procedures via suitable levers, such as for example for spinal rotation in case of deformities, a statement concerning forces or moments to be applied can be made. For example the stiffness of the spinal column can be assessed, and if appropriate further measures for release for an improved correction outcome can be performed. As a result, an uneven in vivo loading of an implant and an uneven loading of body tissues, in particular of soft and/or bone tissue, can be avoided. This particularly advantageously contributes to a long in vivo service life/survival time of an implant.

For example, the trial implant or trial implant part can be selected from the group comprising or consisting of trial joint, trial joint part, trial joint head or trial joint head part, trial joint socket or trial joint socket part, trial joint insert or trial joint inlay, in particular trial cup inlay, trial hip joint, trial hip joint part, trial hip joint head or trial hip joint head part, trial hip joint socket or trial hip joint socket part, trial sliding surface, trial joint sliding surface, trial tibia and trial femur.

If for example the two compartments of a knee arthroplasty trial sliding surface discolor differently, that is an indication to the user, preferably doctor, that the lateral and medial ligament tension are still differently set. Through the different colors or color changes, he obtains the information as to which side is tighter and which side looser. In the case of a trial femur, the position and alignment of the patella during the bending/stretching and thus the correct position of the patella in relation to a femur implant can be determined.

In a further embodiment, the trial implant or trial implant part is a trial implant for the spinal column, i.e. a so-called spinal trial implant, preferably an intervertebral trial implant, or a trial implant part for the spinal column, i.e. a so-called spinal trial implant part, preferably an intervertebral trial implant part. Such a trial implant or trial implant part can particularly advantageously after insertion yield information on the contact area and in particular on possible loading peaks.

In a further embodiment the trial implant is a meniscus trial implant. Preferably, the meniscus trial implant has at least one articulation surface, in particular one or two articulation surfaces, for effecting an articulation with a femur (thigh bone) and at least one articulation surface, in particular one or two articulation surfaces, for effecting an articulation with a tibia (shin bone). Preferably, the at least one articulation surface for effecting an articulation with a femur and/or the at least one articulation surface for effecting an articulation with a tibia contain a mechanophore or are provided with a coating which contains a mechanophore. Thereby in particular an assessment is possible as to whether the forces acting in vivo on the articulation surfaces are of equal magnitude.

In an alternative embodiment, the medical product is a medical, in particular surgical, instrument or instrument part, preferably a human medical, in particular human surgical, instrument or instrument part.

The instrument or instrument part can in particular be a single-use instrument or single-use instrument part.

The instrument or instrument part can in particular be an instrument or instrument part for force indication, in particular for torque or spreading force indication For example the instrument can be a torque wrench. The attainment of a required torque or the exceeding of the same can for example particularly advantageously be made visible by different coloration of the mechanophore.

In a further embodiment, the instrument is a spreader.

In a further embodiment, the instrument is an instrument, in particular spreader, with a solid body joint. In the sense of the present invention, the expression "solid body joint" should be understood to mean a region of a medical, in particular surgical, instrument which allows a relative movement between two rigid body regions of the instrument by bending. The solid body joint is designed to undertake the function of a conventional joint or bearing. Preferably, the solid body joint is configured as a smooth pivot. Such a joint can replace a conventional pivot joint and enable a certain swiveling between two rigid regions of the instrument. The solid body joint can for example be configured as a leaf spring joint, notch joint, triangular joint, cartwheel joint, parallel joint or cruciform spring joint.

Preferably, the solid body joint, in particular only the solid body joint, contains the mechanophore. In this manner a kind of "force indication" can particularly advantageously be implemented. This can for example be used in the determination of joint gaps in the context of a knee endoprosthetic treatment, in order always to apply the same force during the expansion of the stretching and bending gap in the medial and lateral compartment of the joint. In this manner, uniform and in particular parallel gaps can be obtained which in turn is advantageous for a long service life of the implants. The embodiment described in this paragraph can further be of advantage in spinal column operations. In such operations, an expansion is also necessary, namely an expansion of the intervertebral region in order to determine the correct implant size and to apply the implant. A further advantage of a spreader or instrument with a solid body joint consists in the possibility of warning of fatigue fractures. Solid body joints which contain the mechanophore or consist of such a compound can moreover be produced more inexpensively and can without difficulty replace conventional joints in surgical instruments. Overall, this results in cheaper production of instruments with solid body joints. This applies particularly strongly in the production of single-use instruments. A further advantage of a solid body joint with the mechanophore provided according to the invention consists in the possibility of indicating that a forbidden sterilization has been performed, and thus to prevent the reuse of single-use instruments.

In a further embodiment, the medical product according to the invention is a solid body joint for a medical, in particular surgical, instrument, preferably for a human medical, in particular human surgical, instrument. Concerning further features and advantages of this embodiment, reference is made to the explanations made in the previous paragraphs.

In a further embodiment, the instrument is a navigation instrument. This is as a rule an elongated instrument. Particularly advantageously, deformations occurring on navigation instruments can be registered through the presence of the mechanophore optionally corrected during the tracking (during the manual tracking).

In a further embodiment, the instrument is a retractor. In the sense of the present invention, the expression "retractor" should be understood to mean a surgical instrument with the aid of which the access to an operation field is held open or else first enabled. The retractor can for example be a retractor for the spinal column, in particular for the lumbar spinal column, or a retractor for hip endoprosthesis (so-called hip retractor).

The retractor preferably has a rack, two retractor arms and two retractor blades. The rack is preferably configured in the form of a linear toothed rack.

Preferably one of the retractor arms is connected to one end of the rack, in particular immovably connected. The other retractor arm is preferably mounted movably along the rack, preferably via a guide sleeve. The two retractor arms each preferably project vertically from the rack. In other words, the retractor arms preferably run parallel to one another. Advantageously, the two retractor arms have the same length. The two retractor arms can each further be subdivided into sections, in particular two sections which are connected together via a joint. Preferably both retractor arms at their ends projecting from the rack each have a fastening device, preferably a hook-shaped fastening device, for fastening the retractor blades on the retractor arms. The retractor blades and the retractor arms are preferably configured such that fastening of the retractor blades on the retractor arms is effected by means of a locking mechanism, in particular a so-called "ball-snap" mechanism. The retractor described in this paragraph is particularly suitable for the lumbar spinal column.

In the retractor described in the previous paragraph, in principle all or only individual retractor components can contain the mechanophoric material or consist of this material. For example, in particular the rack, at least one of the two retractor arms and/or at least one of the two retractor blades can contain the mechanophoric material or consist of the mechanophoric material. However, according to the invention it is preferable if only the two retractor blades or at least one of the two retractor blades contains the mechanophoric material or consists of this material.

In an alternative embodiment, the retractor is a curved instrument with a convex contact surface, wherein the instrument has on the distal side a tip, for example a sharp tip, blunt tip, short tip, V-shaped tip, U-shaped tip or a femoral neck tip.

In a further embodiment, the medical product is a bone replacement material, in particular a bone cement. In this embodiment, the medical product can for example further contain polymethyl methacrylate as polymer. Polymethyl methacrylate is usable in joint endoprosthesis in particular for anchoring implants on the bone. Preferably, the polymethyl methacrylate and the mechanophore form a mixture of the medical product. The mechanophore can particularly advantageously indicate an overloading of the bone replacement material, in particular of the bone cement. As a result, laborious colorizing of the bone replacement material can be omitted. Additionally, tensions and elongations which have not yet resulted in fissures in the bone replacement material, in particular bone cement, can be made visible. According to the invention, it can further be provided that the bone replacement material before its implantation is tested ex vivo for its resilience, in particular mechanical resilience. For this, for example the mechanophore can be added to a bone cement material in laboratory experiments.

According to a second aspect, the invention relates to the use of a mechanophore for a medical product, preferably trial implant or trial implant part, or for producing a medical product, preferably trial implant or trial implant part. Concerning further features and advantages, in particular of the polymer, of the mechanophore, of the trial implant or trial implant part, and of the medical product, for the avoidance of unnecessary repetitions, complete reference is made to the statements made in the context of the first aspect of the invention.

Further features and advantages of the invention follow from the following description of preferred embodiments in the form of practical examples, the diagrams relating thereto and the claims. Here the features can each be implemented for themselves alone or in combination with one another. The embodiments described below serve only for the explanation and for better understanding of the invention and are in no way to be understood as limiting.

DETAILED DESCRIPTION OF FIGURES

Figure 1:
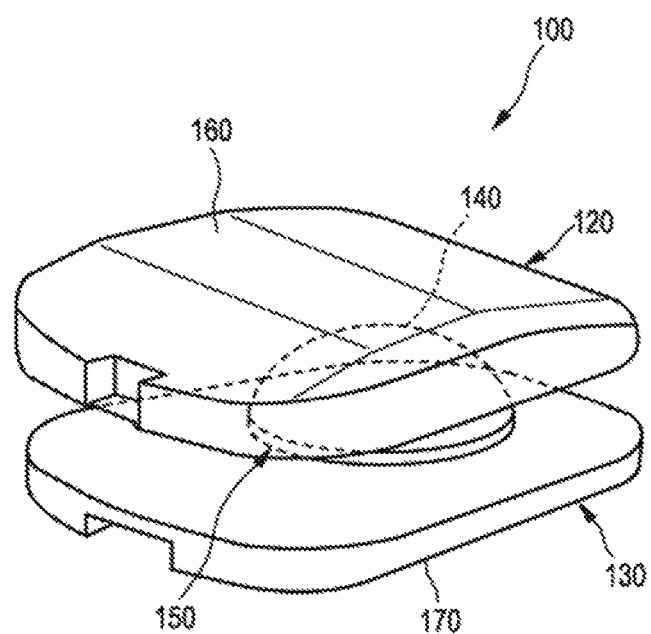
FIG. 1 shows an embodiment of a medical product according to the invention in the form of an intervertebral trial implant, FIGS. 2a to 2c further embodiments of a medical product according to the invention each in the form of a trial implant,
FIG. 3 a further embodiment of a medical product according to the invention in the form of a surgical instrument with a solid body joint,
FIGS. 4a to 4f various embodiments of a medical product according to the invention each in the form of a solid body joint,
FIG. 5 a further embodiment of a medical product according to the invention in the form of a retractor and
FIG. 6 a further embodiment of a medical product according to the invention in the form of a retractor.

FIG. 1 shows diagrammatically an embodiment of a medical product according to the invention in the form of an intervertebral trial implant 100.

The intervertebral trial implant 100 comprises an upper contact element 120 and a lower contact element 130. The two contact elements 120 and 130 are preferably made approximately plate-shaped. Both contact elements 120 and 130 lie flat on one another on bearing surfaces. For this, the lower contact element 130 has a convex, spherical, bearing surface 140 projecting upwards which inserts into a complementary, concave bearing surface 150 on the underside of the upper contact element 120. As a result, the two contact elements 120 and 130 are swivelable relative to one another, so that the mutual inclination of their outer sides 160 and 170 which run essentially parallel, is adjustable. The outer sides 160 and 170 form contact surfaces on adjacent vertebral bodies when the intervertebral trial implant 100 is pushed into an intervertebral space between the two vertebral bodies (not shown).

For the assessment of the forces which act on an intervertebral implant in vivo, the intervertebral trial implant 100 contains a mechanophore.

In principle, all components or only individual components of the intervertebral trial implant 100, such as for example the upper contact element 120, the bearing surface 150, the lower contact element 130 and/or the bearing surface 140, can contain a mechanophore.

The mechanophore is preferably a component of a mixture, wherein the mixture as well as the mechanophore can in particular contain a polymer, such as for example polymethyl methacrylate. The mixture can in particular be a coating of the intervertebral trial implant.

Figure 2A:
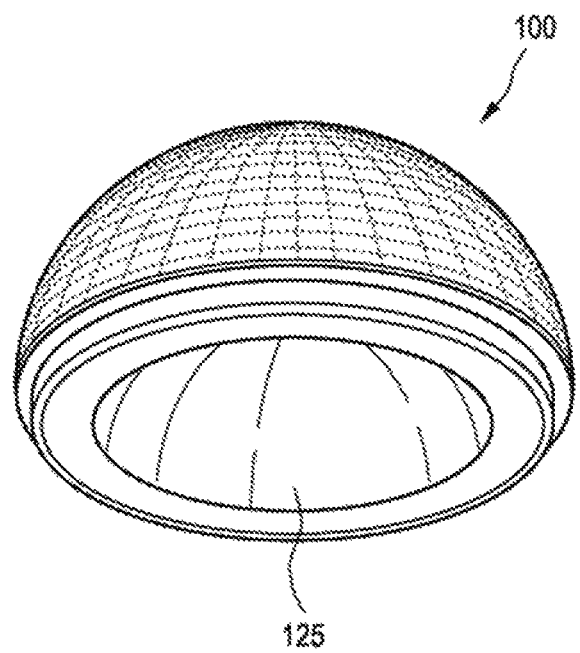

FIG. 2a shows a further embodiment of a medical product according to the invention in the form of a trial implant 100.

The trial implant 100 is configured as a trial joint socket, in particular trial hip joint socket, with a sliding surface 125.

In principle, all regions of the trial implant 100 or only individual regions thereof can contain a mechanophore, in particular a mixture with a mechanophore or a coating with a mechanophore. According to the invention it is preferable if only the sliding surface 125 of the trial joint socket 100 contains a mechanophore, in particular is provided with a coating which contains a mechanophore.

The trial joint socket shown FIG. 2a serves for the assessment of forces which act in vivo on an artificial joint socket, in particular artificial hip joint socket.

Figure 2B:
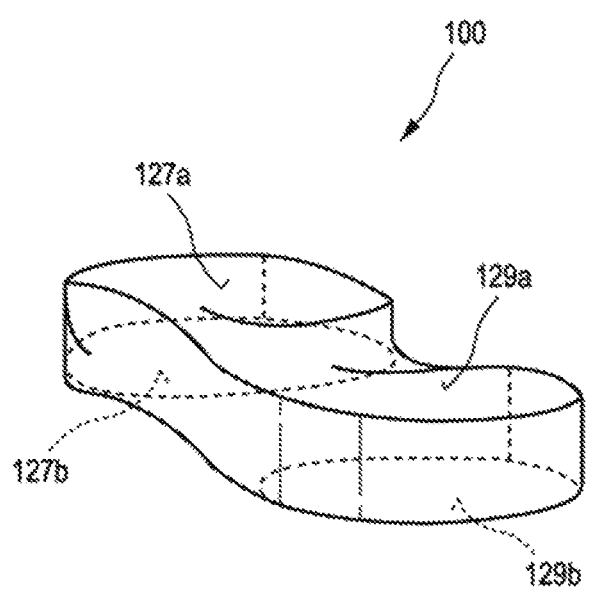

FIG. 2b shows a further embodiment of a medical product according to the invention in the form of a trial implant 100.

The trial implant 100 possesses two articulation surfaces 127a and 129a for effecting an articulation with a femur and two articulation surfaces 127b and 129b for effecting an articulation with a tibia.

The articulation surfaces 127a and 129a and the articulation surfaces 127b and 129b can each be configured the same (so-called symmetrical meniscus trial implant). Alternatively, the articulation surfaces 127a and 129a and the articulation surfaces 127b and 129b respectively can be configured differently (so-called asymmetrical meniscus trial implant).

The trial implant 100 is suitable for the assessment of forces which act on an artificial meniscus implant in vivo.

In principle, all regions or only individual regions of the trial implant 100 can contain a mechanophore, in particular be provided with a coating containing a mechanophore. According to the invention, it is preferable if only the articulation surfaces 127a, 129a, 127b and 129b contain a mechanophore, in particular are provided with a coating containing a mechanophore. As a result, an assessment is possible as to whether the forces acting in vivo on the articulation surfaces 127a, 129a, 127b and 129b are of equal magnitude.

Figure 2C:
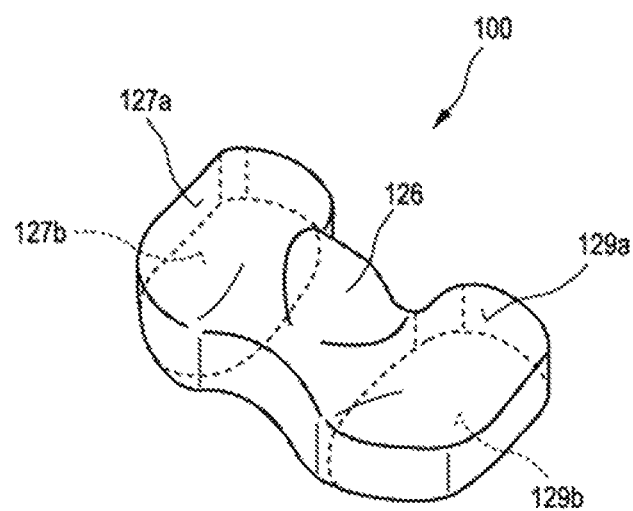

FIG. 2c shows a further embodiment of a medical product according to the invention in the form of a trial implant 100.

The trial implant 100 has two articulation surfaces 127a and 129a for effecting an articulation with a femur and two articulation surfaces 127b and 129b for effecting an articulation with a tibia.

The articulation surfaces 127a and 129a and the articulation surfaces 127b and 129b can each be configured the same (so-called symmetrical meniscus trial implant). Alternatively, the articulation surfaces 127a and 129a and the articulation surfaces 127b and 129b respectively can be configured differently (so-called asymmetrical meniscus trial implant).

Furthermore, the trial implant has a post 126. The post is also configured for an articulation with a femur. For this, the post 126 must be able to accommodate translational forces. The post 126 is positioned between the articulation surfaces 127a and 129a.

The trial implant 100 shown in FIG. 2c also serves for the assessment of forces which act on an artificial meniscus implant in vivo.

In principle, all regions or only individual regions of the trial implant 100 can contain a mechanophore, in particular be provided with a coating containing a mechanophore.

According to the invention it is preferable if only the articulation surfaces 127a, 129a, 127b and 129b and/or the post 126 contain a mechanophore, in particular are provided with a coating which contains a mechanophore. As a result, an assessment is possible as to whether the forces acting in vivo on the articulation surfaces 127a, 129a, 127b and 129b are of equal magnitude and/or forces acting in vivo remain below a limit value, the exceeding of which would result in deformation or destruction, in particular breakage of the post 126.

Figure 3:
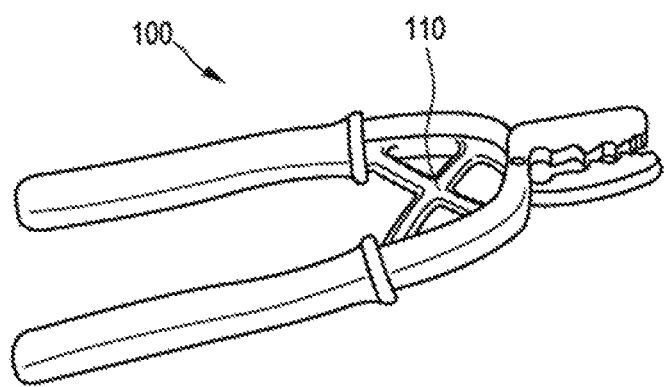

FIG. 3 shows an embodiment of a medical product according to the invention in the form of a medical instrument 100. The instrument 100 is embodied as grasping forceps with a cartwheel-shaped solid body joint 110. The solid body joint 110 contains a mechanophore. The solid body joint 110 can in particular be provided with a coating which contains a mechanophore. In this manner, a type of "force indication" can particularly advantageously be implemented. Such a force indication can be advantageous for example in the determination of joint gaps in the context of a knee endoprosthetic treatment, in order always to apply the same force in the expansion of the extension and bending gap in the medial and lateral compartment of the joint.

FIGS. 4a to 4f each show one embodiment of a medical product, in each case in the form of a solid body joint 110.

Figures 4A, 4B, 4C:
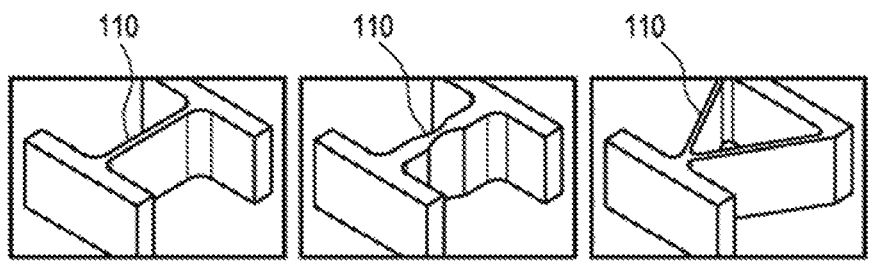

The solid body joint 110 shown in FIG. 4a is a leaf spring joint.

The solid body joint 110 shown in FIG. 4b is a notch joint.

The solid body joint 110 shown in FIG. 4c is a triangular joint.

Figures 4D, 4E, 4F:
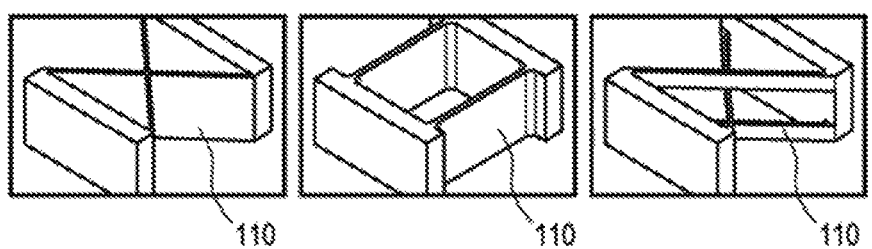

The solid body joint 110 shown in FIG. 4d is a cartwheel joint.

The solid body joint 110 shown in FIG. 4e is a parallel joint.

The solid body joint 110 shown in FIG. 4f is a cruciform spring joint.

The solid body joints 110 shown in FIGS. 4a to 4f in each case contain a mechanophore. In particular, the solid body joints shown in FIGS. 4a to 4f can in each case be provided with a coating which contains a mechanophore.

Figure 5:
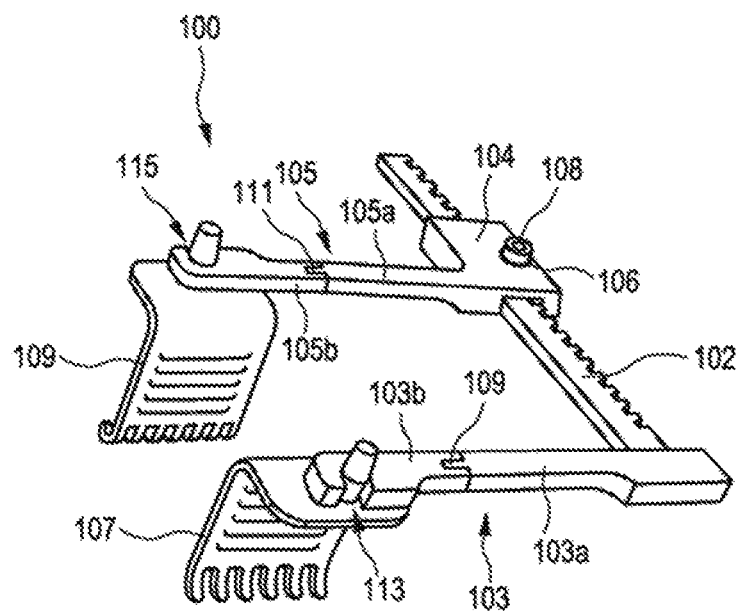

FIG. 5 shows a further embodiment of a medical product according to the invention in the form of a retractor 100.

The retractor 100 comprises a rack 102, two retractor arms 103 and 105 and two retractor blades 107 and 109.

The rack 102 is in the form of a linear toothed rack.

The toothed rack 102 is connected at one end to the retractor arm 103, preferably immovably. The retractor arm 103 projects vertically from the toothed rack 102.

On the toothed rack 102, the second retractor arm 105 is mounted movably along the toothed rack 102 via a guide sleeve 104. The retractor arm 105 runs parallel to the retractor arm 103 and has the same length as the retractor arm 103.

For fixation of the retractor arm 105 at a defined distance from the retractor arm 103, the guide sleeve 104 has a set-screw 106. The set-screw 106 has on its outside a hexagon socket 108 to accommodate a turning tool.

The retractor arm 103 is subdivided into two sections 103a and 103b which are connected together via a joint 109. Correspondingly, the retractor arm 105 is subdivided into two sections 105a and 105b which are connected together via a joint 111.

The two retractor arms 103 and 105 at their ends projecting from the toothed rack 102 each have a hook-shaped fastening device 113 and 115 for fastening the retractor blades 107 and 109. Preferably, the retractor blades 107 and 109 and the retractor arms 103 and 105 are configured such that fastening of the retractor blades 107 and 109 on the retractor arms 103 and 105 is effected by a "ball-snap" mechanism.

To limit tissue retraction forces, it is preferable if at least one of the two retractor blades 107 and 109, preferably both retractor blades 107 and 109, contain a mechanophore, in particular are provided with a coating which contains a mechanophore.

The retractor shown in FIG. 5 is especially suitable for the lumbar spinal column.

Figure 6:
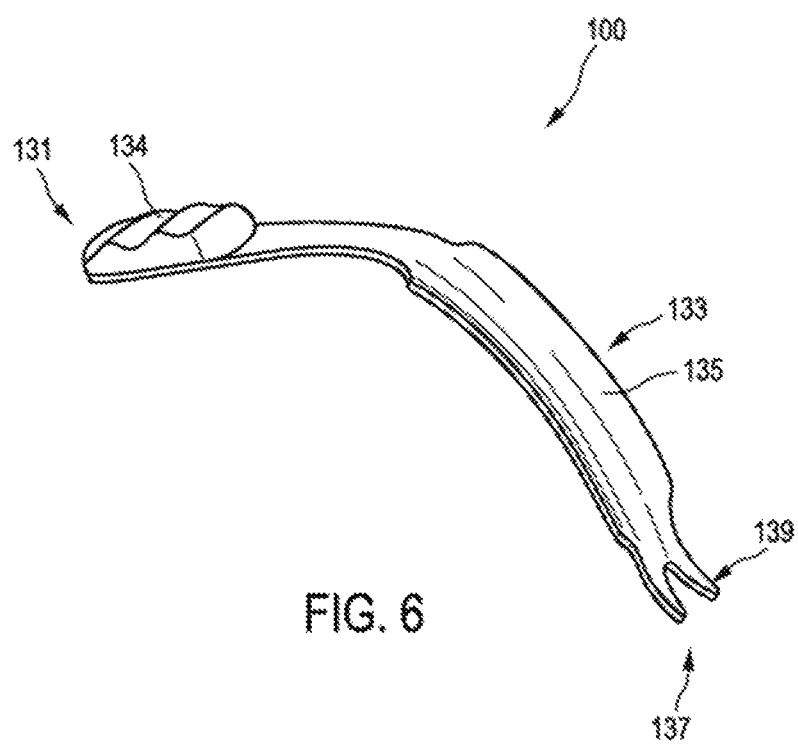

FIG. 6 shows a further embodiment of a medical product according to the invention 100 in the form of a retractor.

The retractor 100 has a section 133 with a convex contact surface 135. The section 133 is designed curved at least in some sections. Depending on the degree of bending of the section 133, the retractor can be used for the presentation of an acetabulum or for the presentation of a femur.

The section 133 ends at a distal end 137 of the retractor 100 in a U-shaped tip 139. To facilitate handling, the retractor can have a handgrip 134 at its proximal end 131. Alternatively, the retractor can have at its proximal end 131 a non-curved, in particular straight, section which takes on the function of a handgrip (not shown).

Particularly in the region of its U-shaped tip 139, the retractor 100 can contain a mechanophore, in particular be provided with a coating which contains a mechanophore.

Concerning further features and advantages of the medical product shown in the diagrams, complete reference is made to the above description.

PRACTICAL EXAMPLES

1. Production of a Trial Knee Joint Inlay

A mixture of polymethyl methacrylate and 3-(4-methoxy-phenyl)-3-(3-methyl-4-methoxyphenyl)-13-hydroxy-indeno[2,1-f]naphto[1,2-b]pyran was melted and poured into a mold which corresponded to the trial knee joint inlay to be produced. After curing of the mixture, the trial inlay was demolded.

2. Production of a Trial Hip Joint Sliding Surface

A mixture of polymethyl methacrylate and piroxicam was melted and poured into a rectangular mold of appropriate size. After curing of the mixture, a trial hip joint sliding surface was then milled out of the solid body by means of a CNC milling machine.

3. Production of a Solid Body Joint

A mixture of polymethyl methacrylate and 3-(4-methoxy-phenyl)-3-(3-methyl-4-methoxyphenyl)-13-hydroxy-indeno[2,1-f]naphto[1,2-b]pyran was melted and poured into a rectangular mold of appropriate size. After curing of the mixture, a solid body joint was then milled out of the solid body by means of a CNC milling machine, and was then used in a spreader instrument.

The invention claimed is:

1. A medical product containing a mechanophore, wherein the medical product is an implant, wherein the implant is a joint prosthesis or wherein the medical product is an implant part, wherein the implant part is a part of a joint prosthesis.

2. The medical product as claimed in claim 1, characterized in that the mechanophore is a component of a mixture or composition of the medical product.

3. The medical product as claimed in claim 1, characterized in that the medical product, in particular the mixture or composition, further contains a polymer.

4. The medical product as claimed in claim 3, characterized in that the polymer is selected from the group comprising polyolefins, polyethylene (PE), ultrahigh molecular weight polyethylene (UHMWPE), polyvinyl chloride (PVC), polyvinylidene chloride, polyvinyl fluoride, polyvinylidene fluoride, polytetrafluorethylene (PTFE), polystyrene, polyvinyl alcohol (PVA), polyacrylic acid or polyacrylate, polymethacrylic acid or polymethacrylate, polymethylmethacrylic acid or polymethyl methacrylate, polydimethylsiloxane, polyurethanes, amorphous polymers, elastomers, thermoplastic elastomers, polypropylene, polytetrafluoropropylene, polyhexafluoropropylene, polyethylene glycol, polypropylene glycol, polyester, polyethylene terephthalic acid or polyethylene terephthalate, polypropylene terephthalic acid or polypropylene terephthalate, polybutylene terephthalic acid or polybutylene terephthalate, polyhydroxyalkanoic acids or polyhydroxyalkanoates, polylactic acid or polylactide, polyglycolic acid or polyglycolide, polyhydroxybutyric acid or polyhydroxybutyrate, poly-3-hydroxybutyric acid or poly-3-hydroxybutyrate, poly-4-hydroxybutyric acid or poly-4-hydroxybutyrate, polytrimethylene carbonate, poly-ε-caprolactone, poly-para-dioxanone, copolymers and mixtures, in particular blends, thereof.

5. The medical product as claimed in claim 3, characterized in that the mechanophore is not covalently linked to the polymer.

6. The medical product as claimed in claim 1, characterized in that the mechanophore is a mechanochromic compound, wherein when undergoing stress the compound undergoes a color-producing or color-changing structural change.

7. The medical product as claimed in claim 6, characterized in that the structural change is accompanied by ring opening of the mechanophore.

8. The medical product as claimed in claim 6, characterized in that the structural change is reversible, in particular under the action of light, preferably UV light.

9. The medical product as claimed in claim 1, characterized in that the mechanophore is selected from the group comprising pyrans, oxazines, fulgides, fulgimides, diarylethylenes, dimeric lactones, dimeric imidazoles and mixtures thereof.

10. The medical product as claimed in claim 1, characterized in that the joint prosthesis is selected from the group comprising knee joint prosthesis, hip joint prosthesis, ankle joint prosthesis, shoulder joint prosthesis, mandibular joint prosthesis, elbow joint prosthesis, finger joint prosthesis and spinal facet prosthesis.

\* \* \* \* \*